(12) United States Patent
Mauze et al.

(10) Patent No.: US 6,939,721 B2
(45) Date of Patent: Sep. 6, 2005

(54) FLUORESCENCE IMMUNOASSAYS USING ORGANO-METALLIC COMPLEXES FOR ENERGY TRANSFER

(75) Inventors: Ganapati R. Mauze, Sunnyvale, CA (US); Dan-Hui Yang, Sunnyvale, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 87 days.

(21) Appl. No.: 09/740,660

(22) Filed: Dec. 18, 2000

(65) Prior Publication Data

US 2002/0076830 A1 Jun. 20, 2002

(51) Int. Cl.$^7$ ............... G01N 33/545; G01N 33/552; G01N 33/533
(52) U.S. Cl. ............... 436/531; 436/527; 436/546; 436/800; 436/805; 436/829
(58) Field of Search ............... 436/527, 531, 436/546, 800, 805, 829, 806

(56) References Cited

U.S. PATENT DOCUMENTS

| | | | | |
|---|---|---|---|---|
| 4,372,745 A | * | 2/1983 | Mandle et al. | 436/537 |
| 5,521,289 A | * | 5/1996 | Hainfeld et al. | |
| 5,631,169 A | | 5/1997 | Lakowicz et al. | 436/537 |
| 6,528,165 B2 | * | 3/2003 | Chandler | 428/402.2 |

FOREIGN PATENT DOCUMENTS

WO          00/32044    *   6/2000

OTHER PUBLICATIONS

Jiyan Chen and Paul R. Selvin, "Thiol–Reactive Luminescent Chelates of Terbium and Europium", Bioconjugate Chem., 1999, 10, 311–315.

Gerard Mathis, "Rare Earth Cryptates and Homogenous Fluorimmunoassays with Human Sera", Clin. Chem., 39(9), 1993, 1953–1959.

Gerard Mathis, "Probing Molecular Interactions with Homogenous Techniques Based on Rare Earth Cryptates and Fluorescenc Energy Transfer", Clin. Chem. 41(9), 1995, 1391–1397.

P. Aich, et al., "M–DNA: A Complex Between Divalent Metal Ions and DNA which Behaves as a Molecular Wire", J. Mol. Biol 1999, 294, 477–485.

Y. Zhou, et al., "Preparation of Hyperbranched Polymer Films Grafted on Self–Assembled Monolayers", J. Am. Chem. Soc. 118 (1996) 3773–3774.

Ilkka Hemmila, t al., "Time–resolved Fluorometry: An Overview of the Labels and Core Technologies for Drug Screening Applications", DDT vol. 2, No. 9, Sep. 1997, 373–381.

Edward M. Kober, et al., "Synthetic Control of Excited States. Nonchromophoric Ligand Variations in Polypyridyl Complexes of Osmium (II)". Inorg. Chem. 1985, 24, 2755–2763.

* cited by examiner

*Primary Examiner*—Mary E. Ceperley
(74) *Attorney, Agent, or Firm*—Timothy H. Joyce

(57) ABSTRACT

The invention includes a composition of matter and method that utilizes energy transfer between one or more donor and acceptor molecules. The composition of matter includes an encapsulation vesicle having a matrix, a surface coating of an organo-metallic complex and a transparent protection layer. The transparent protection layer is capable of modification by addition of biomolecules to the surface in order to bind other molecules. The proximity of the bound biomolecules to the protective layer allows for energy transfer from a donor molecule internal to the protection layer to an acceptor molecule outside the protection layer. The protection layer acts to diminish the effects of collisional quenching on the donor molecules caused by ubiquitous small molecules such as molecular oxygen. The application also teaches a method of making and applying the complexes to immunoassays.

38 Claims, 4 Drawing Sheets

ENZYME ACTION

FLUORESCENCE IMMUNOASSAYS USING ORGANO-METALLIC COMPLEXES FOR ENERGY TRANSFER

FIELD OF THE INVENTION

This invention relates to fluorescence immunoassays, DNA hybridization assays, and more particularly to a composition of matter and method for using organo-metallic complexes for assays that can be easily quenched by interfering molecules in energy transfer processes.

BACKGROUND OF THE INVENTION

Fluorescence immunoassays based on energy transfer have been taught by Lakowicz et al. in U.S. Pat. No. 5,631,169. A number of molecular species have been used for causing energy transfer from a donor molecule to an acceptor molecule. In particular, sandwich type immunocomplex formation can be used with this technique. For instance, this technique can be used for immunoassays based on changes in fluorescence lifetime with changing analyte concentration. However, this technique works with short lifetime dyes like fluorescein isothiocyanate (FITC) (the donor) whose fluorescence is quenched by energy transfer to Eosin (the acceptor). A problem or disadvantage of this technique is that short lifetimes are extremely difficult to measure. Moreover, the donors used in this invention have relatively short Stoke shifts, which could cause excitation signal to overlap the acceptor absorption thereby causing spurious signals, particularly when broad band emitters like LEDs are used as excitation sources.

Organo-metallic complexes can be used as donors without identifying suitable acceptors. However, there are a number of small molecules such as oxygen that also quench fluorescence of these complexes. For these reasons a number of problems exist when using some of the standard organo-metallic complexes for quenching experiments, measurements or immunoassay studies. Organo-metallic complexes, however, have the advantage of providing more suitable long lifetime based sensing and quenching. Consequently, assays based on this principle would require that the sample be purged of oxygen prior to analysis. This not only adds an additional sample preparation step, but also precludes one from analyzing samples that could be altered by such processing.

Accordingly, there is a substantial need for techniques and compositions of matter that allow for the use of a long lifetime donors to be used in conjunction with immunoassays based on the use of energy transfer. In addition, there is a need for donors that will allow for larger Stoke shifts, but not suffer from the limitation of quenching by molecules such as molecular oxygen. Furthermore, there is a need for techniques and compositions of matter that allow for the use of organo-metallic complexes that can be applied in the presence of changing concentration of collisional quenchers.

The above reference(s) and all other references cited in this application are incorporated in this application by reference. However, cited references or art are not admitted to be prior art to this application.

SUMMARY OF THE INVENTION

The invention provides a composition of matter and method of using the same for immunoassays. The encapsulation vesicle comprises a matrix, a surface coating with an organo-metallic complex and a transparent protection layer. The protection layer is capable of modification by addition of biomolecules to the exterior surface. The biomolecules may comprise one or more acceptor molecules. The proximity of the bound biomolecules to the protection layer allows for energy transfer from donor molecules that are inside of the transparent protection layer to the acceptor molecules that are outside the transparent protection layer. The transparent protection layer acts to diminish the effects of collisional quenching by small molecules such as oxygen to the donor molecules. The method includes a number of novel immunoassays that utilizes energy transfer between one or more donor and acceptor molecules.

BRIEF DESCRIPTION OF THE DRAWINGS

Embodiments of the invention will now be described with reference to the drawings in which.

DETAILED DESCRIPTION OF THE INVENTION

Figure 1:
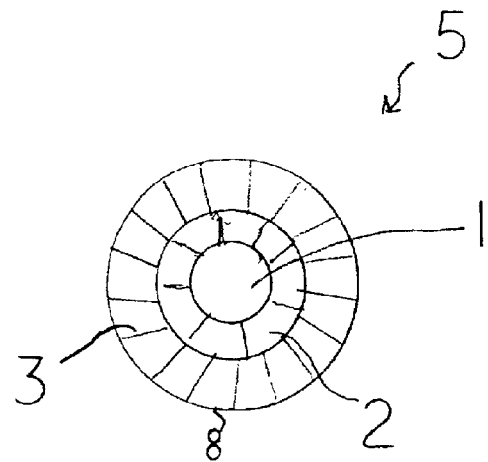
FIG. 1 illustrates a first embodiment and cross-section of the composition of matter of the present invention.

Before describing the present invention in detail, it is to be understood that this invention is not limited to specific compositions, process steps, or equipment, as such may vary. It is also to be understood that the terminology used herein is for the purpose of describing particular embodiments only, and is not intended to be limiting.

It must be noted that, as used in this specification and the appended claims, the singular forms "a", "an", and "the" include plural referents unless the context clearly dictates otherwise. Thus, for example, reference to "an assay", includes more than one assay, reference to a "matrix" includes a plurality of matrixes and the like.

In describing and claiming the present invention, the following terminology will be used in accordance with the definitions set out below.

The term "acceptor" shall refer to any molecule or complex capable of receiving energy emitting from a donor molecule or complex. Acceptor molecules may comprise any compounds whose absorption spectrum has substantial overlap with the emission spectrum of the donor molecule. For instance, fluorescein, Cy5 and allophycocyanine could be used as acceptors for lanthanide; fast green and light green yellowish could be efficient acceptors for most of the ruthenium complexes.

The term "donor" shall refer to any molecule or complex capable of emitting energy such that the emission spectrum substantially overlaps the absorption spectrum of the acceptor.

The term "matrix" includes a complex or material capable of supporting other materials. This material may include gels, porous network materials, organic and inorganic polymers, and biomaterials. In particular, the term refers to a complex made of sol-gel material.

The term "surface coating" refers to a thin film or layer applied to a matrix material and shall include both known and unknown organo-metallic compounds and elements capable of acting as energy donors. For purposes or this invention, the above term shall also include the situation when the donor is distributed in the entire matrix and parts thereof. In such a situation, at least a small fraction of the donor near the surface of matrix will participate in the energy transfer process.

The term "protection layer" refers to a material, film, layer, or complex that is transparent or translucent and may allow energy to pass through it. In particular, this layer need not be completely contiguous, but it must be capable of preventing quencher molecules from reaching the acceptor molecules of the surface coating.

The term "ligand" shall refer to any molecule, small molecule, protein, antibody, antigen or biomolecule capable of binding other molecules. The term biolmolecule shall include proteins, DNAs, RNAs, polypeptides, and receptor molecules.

According to this invention a long lifetime donor such as ruthenium tris diphenyl phenanthroline is sequestered or absorbed on a surface such as a silica particle. The surface with the absorbed donor layer is then coated with a layer of optically transparent matrix such as sol gel, which also acts as a diffusion barrier to quenchers such as oxygen. Thus, the donor molecule is trapped in a composite structure (referred to as a donor particle). The donor can be excited by appropriate radiation transmitted through the transparent barrier layer. Moreover, the transparent barrier allows fluorescence emission from the donor to radiate through it.

The donor surface can be functionalized to immobilize a recognition element such as an antibody that complexes with the analyte of interest. Such an antibody tagged with a donor molecule can be used in competitive immunoassays in a few different ways discussed below.

CONSTRUCTION OF THE ENCAPSULATION VESICLES

EXAMPLE 1

Ruthenium tris disphenyl phenanthroline was purchased from GFM Chemicals (Catalog No. 2355, Lot #L027182). Silica (CAB-0-sil, TS-720) or hydrophobic amorphous fumed silica, was purchased from Cabot corporation. Approximately 20 ml's of saturated chloroform solution of the ruthenium complex was prepared. 0.5 grams of hydrophobic silica was added to this dye solution. The mixture was then stirred for approximately four hours until it appeared to be homogenous. Next, filtration was carried out and the silica particles were then washed with acetone. Washing need not be completely efficient at this step since the filtration rate was extremely slow while the evaporation of the solvent was relatively fast. The dried silica particles were then ground.

The ruthenium encapsulated silica beads were put in a vial and 1 ml of sol solution of the following composition was added: 3.0 ml tetramethoxy silane, 1.2 ml water, 2 ml methanol and 0.4 ml 0.1 N hydrochloroic acid. The mixture was stirred and substantially agitated for around four hours, until a viscous solution was reached. The product was then transferred onto filtration paper and allowed to dry under ambient conditions. The final dried produce was then ground and stored.

EXAMPLE 2

0.5 grams of fumed hydrophobic silica (from Cabot) was suspended in saturated solution of $Ru(Ph_2Phen)_3 \cdot 2BPh_4$ in 4 ml chloroform and 8 ml acetone. The mixtures were well shaken and let to stand at room temperature for a day. The silica particles were centrifuged and washed once with methanol. Then 1 ml, sol-gel solution of the following composition was added: 3.0 ml tetramethoxy silane, 1.2 ml water, 2.0 ml methanol and 0.4 ml 0.1 N hydrochoric acid. The mixture was vortexed for 15 minutes until it became homogenous and then the final product was centrifuged at higher speed for 8 minutes. The supernatant was discarded. The sol-gel protected fluorophore particle was allowed to dry under ambient conditions and then ground.

FIG. 1 shows the composition of the present invention. The invention includes an encapsulation vesicle comprising a matrix 1, a surface coating 2, and a protection layer 3. The protection layer 3 has an exterior surface 8 that may include one or more surface modifications such as a biomolecule. Biomolecules may include the use of an antibody or similar type molecule capable of binding other molecules such as an antigen, or other molecules or proteins with an acceptor molecule.

The matrix 1 may comprise a variety of different materials that are capable of supporting other compounds or materials. The matrix may comprise a hydrophobic material. However, the material must be capable of being modified and or coated by a surface coating 2. Matrix 1, may comprise a silica, sephadex or synthetic polymer type material capable of absorption of solvents. In its preferred embodiment, the material is a sol-gel composition. The sol-gel composition comprises a silica and synthetic polymer composition. The surface of the matrix can be modified with carboxyl and/or amino groups so that the organometallic complexes can be covalently attached. In other words, the surface is modified so that long lifetime fluorophores can be absorbed or covalently linked on the surface of the matrix.

Surface coating 2, may comprise a variety of materials including organic and inorganic molecules. Surface coating 2 must be capable of acting as a donor. In its preferred embodiment, the surface coating 2 comprises a ligand such as an organo-metallic material capable of acting as a donor molecule to a nearby energy acceptor. Organo-metallic materials are particularly effective as energy transfer donors because of their larger stoke shifts and high sensitivity. The organo-metallic materials that are used as donor molecules include ruthenium tris diphenyl phenanthroline complexes. In particular, the ruthenium complexes have maximum emission peaks or spectra at about 650 nm. Europium complexes emit at about 615 nm and terbium complexes emit at about 520 nm. A number of molecules can be used as donors. For instance,

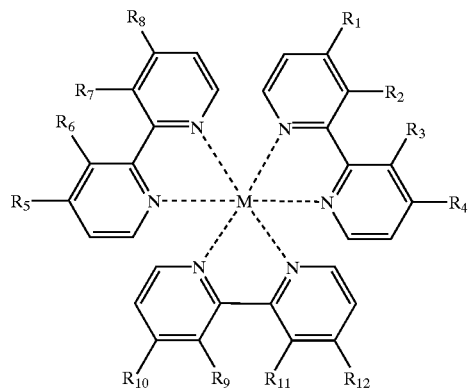

In this complex, the coordination metal may include Ru, Os and Re. These also include materials that can form long lifetime metal-ligand complexes with bipyridine and/or phenanthroline ligands. There are twelve different ligands designated $R_1$–$R_{12}$. These ligands represent H, aryl, alkyl and aryl leading to the formation of non-substituted and substituted phenanthroline. Other donor molecules include:

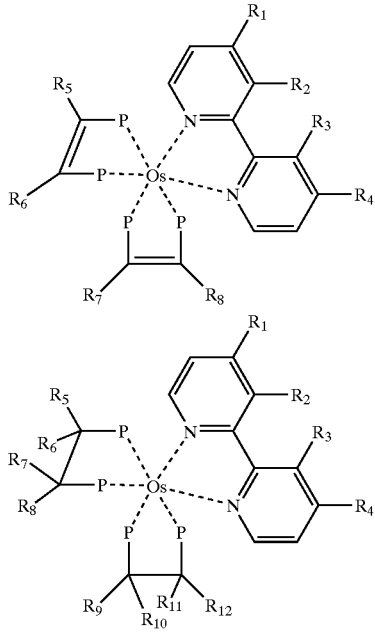

where $R_1$, $R_2$, $R_3$, $R_4$, represent H, alkyl, aryl, aryl leading to the formation of non-substituted or substituted phenanthroline.

$R_5$, $R_6$, $R_7$, $R_8$, $R_9$, $R_{10}$, $R_{11}$, $R_{12}$ represent H, alkyl, aryl, aryl leading to the formation of ortho-aromatic phosphines These fluorophores have a lifetime of greater than 100 ns and are then susceptible to oxygen quenching.

Other long lifetime probes (donors) are lanthanides. These include the complexes of Eu, Th, Sm, Dy. Some examples of complexes with typical ligands are shown below. They can be classified into 3 major groups including: 1, alkyl polycarboxyl complexes with at least one shorter wavelength absorption antenna; 2. polypyridine complexes having ligands with carboxyl groups on or near the coordination site; and 3, polypyridine cryptate complexes. Chemical structures of each are shown for 1–3 (from top to bottom) below.

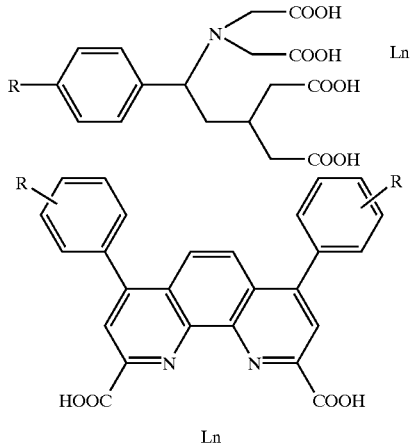

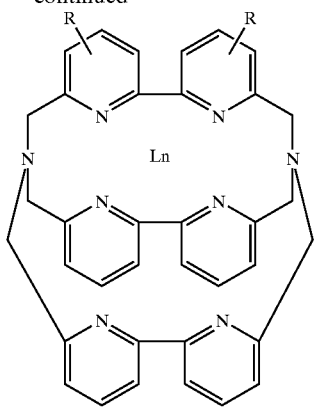

wherein Ln=Eu, Th, Sm, Dy, and R represents H or a functionality capable of covalently linking to a matrix.

Acceptor molecules are different from donors in both composition and function. For instance, the acceptor molecules or complexes can comprise a ligand with a biomolecule. However, it should be noted that the only theoretical requirement is that the acceptor be positioned on or near the outside of the protection layer 3, discussed below, and that the acceptor's absorption band have a fair overlap with the emitting band of the donor. For example, Fast Green and Light Green SF yellowish and others can be used as acceptors for ruthenium complexes. Fluorescein, Cy5 and APC (allophycocyanin, a 105 kD phycobiliprotein) could be used as acceptors for lanthanide probes.

The protection layer 3 is important to the invention because it prevents the donor molecules on the surface coating 2 from being effected by ubiquitous quencher molecules such as oxygen. The most problematic quencher molecules being ubiquitous quenchers that exist in the environment of the acceptor molecules. The protection layer 3 may comprise any number of materials that are capable of excluding small molecule that may cause an effect on the quantum yield of the donor molecules. For instance, the actual protection layer 3 may comprise any number of materials capable of excluding small molecules, yet allow the transfer of energy through the material. To prevent oxygen from diffusing, the surface has to be modified with hydrophilic functionalities, such as hydroxy, carboxy, and protonated amines.

In most cases, this means that the material must be translucent or transparent. It is important that the material be designed in such a way that energy transfer can take place through or in conjunction with the protection layer 3. The protection layer could be sol-gel (silica) and synthetic polymers. To prevent oxygen from diffusing the surface can be modified with hydrophilic functionalities such as hydroxyl, carboxyl, or protonated amines (Zhou, Y. et al. 1996). The protection layer may be formed by the method of suspension polymerization. Protection layer 3 may also contain an antibody or acceptor molecule on its exterior surface. The antibody is capable of binding other small molecules or an antigen. The Antigen may contain an acceptor molecule that is capable of receiving energy from the donor molecule that is on the surface coating 2 inside the protection layer 3. The acceptor molecule and the donor molecule must be sufficiently close in space that the energy transfer can take place from the donor molecule to the acceptor molecule. For instance, if the donor molecule and the acceptor molecule are too far apart then energy transfer will either not take place, or will not be efficient enough to result in the facile measurement. The rate of energy transfer has a $1/r^6$ dependency on distance. The energy transfer will not be significant or possible if the distance between the donor and acceptor is larger than 60–70 angstroms.

The method used in making the encapsulation vesicle is straight-forward. In the first step of the invention the matrix is prepared using the silica particles. Next, a monolayer of the fluorescent dye is added to the particles. The layer is allowed to dry and the protection layer is added to the surface coating.

Figure 2:
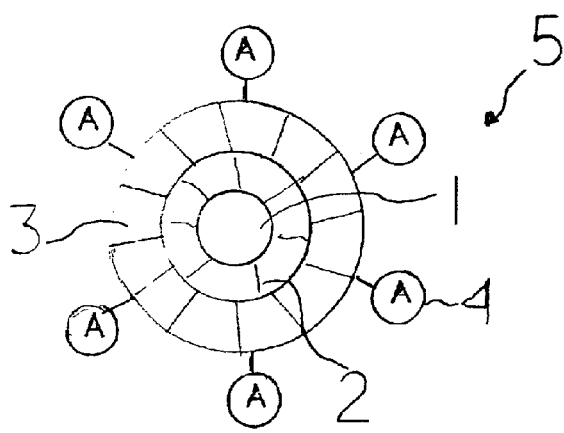
FIG. 2 illustrates a second embodiment and cross-section of the composition of matter of the present invention with acceptor molecules directly attached to the protection layer.

FIG. 2 shows a diagram of a second embodiment of the composition of matter of the present invention. The encapsulation vesicle 5 has the acceptor molecules 4 attached directly to the protection layer 3. The encapsulation vesicle 5 is designed in such a way that the acceptor molecules 4 may receive energy or electrons from the surface coating 2 that contains the donor molecules. This invention provides for ease in monitoring changes in the encapsulation vesicle (s) over time. FIG. 2 shows the simplest case scenario where the acceptor molecule 4 is directly attached to the protection layer 3. However, acceptor molecules 4 need not be attached directly to protection layer 3 and in some cases may actually be free in solution.

Figure 3:
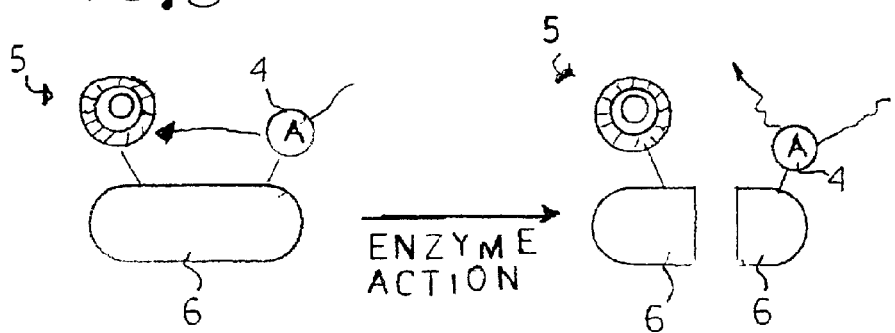
FIG. 3 shows a third embodiment of the composition of matter of the present invention with the acceptor molecules attached to a separate substrate.

FIG. 3 shows a third embodiment of the composition of matter of the present invention. The figure shows the encapsulation vesicle 5 on one end of a substrate 6 and the relationship between the acceptor molecule(s) 4 and the encapsulation vesicles 5. The embodiment includes the use of an enzyme or enzyme action that results in cleavage of the substrate 6 and separation of the encapsulation vesicle 5 from the acceptor or acceptor molecules 4. Cleavage is accomplished by the enzyme and energy transfer is no longer possible between the donor and acceptor.

The method of the present invention (illustrated in FIGS. 4A–4D) is capable of determining and quantifying binding reactions used in immunoassays. In the present method the reactants are labeled with a photoluminescent energy transfer donor and acceptor. The invention differs in that there is a protection step included so as to limit or eradicate the effects of collisional quenchers on the donor complex or molecule. The immunoassay or immuno-reaction brings the donor and acceptor molecules into close proximity. This is important, because when the reaction product is excited through application of an external source, energy transfer can occur between the donor and the acceptor. The present method can be used with a variety of different assays including competitive and non-competitive. In addition, the antigen and/or antibody can be labeled with more than one acceptor molecules.

The method of the present invention includes mixing a first binding molecule with a second binding molecule. The second binding molecule may be free in solution or fixed to a vesicle surface. In other words, the donor and the acceptor are brought into close interacting proximity, and are capable of producing a detectable luminescence lifetime change in the photoluminescence lifetime of the donor. The method also includes the steps of encapsulating the donor molecule so that collisional quenchers such as oxygen will not interfere with energy transfer from the donor to the acceptor, exposing the sample to an exciting amount of radiation and then detecting the resulting emission. Lastly, the apparent luminescent lifetime of the donor is calculated to quantify the binding of the first binding molecule to the second binding molecule.

EXAMPLE 1

In a first embodiment of the invention (See FIG. 4A), a known concentration of analyte (the antigen) of interest, tagged with an acceptor, is incubated with the donor-tagged antibody described above, thus allowing the antibody-antigen immuno-complex to form. After this step is complete, the fluorescence lifetime and/or intensity of fluorescence emitted by the donor, in response to appropriate excitation, are measured. Subsequently, sample is introduced to the above immuno-complexes. Upon appropriate conditioning, the antigen of interest will displace the tagged antigen from the immuno-complex. The number of such displacement events will be proportional to the ratio of the concentration of the antigen in the sample. This will decrease immuno-complexes wherein the donor to acceptor energy transfer occurs. This will result in a net decrease in the lifetime and/or intensity of the donor emission. This increase in lifetime and/or intensity is related to the concentration of the analyte.

The acceptor may be any molecule whose absorption characteristics significantly overlap the emission characteristics of the donor. Selection of the acceptor and the corresponding donor is primarily based on the criteria of overlapping emission-absorption characteristics and the efficiency of the resultant energy transfer. The practice of teaching in several embodiments would be obvious to those familiar with the field of assay design such as fluorometry and fluorophore chemistry.

Figure 4A:
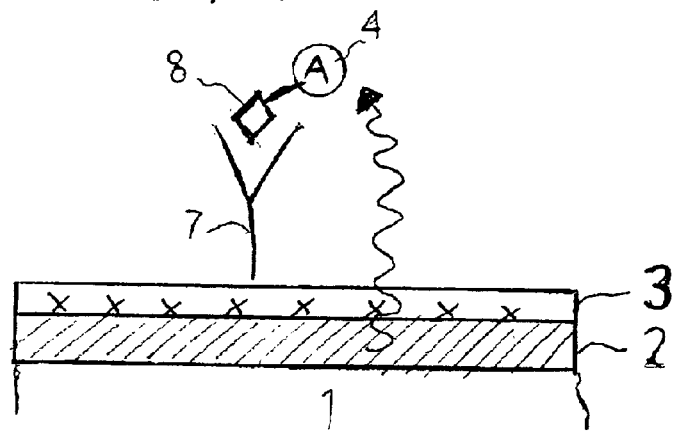
FIG. 4A shows a first embodiment and method of the present invention using a standard immunoassay.

FIG. 4A shows the method of the present invention using standard immunoassay components. In the method, an antibody 7 is linked to the protection layer 3 that encapsulates the surface coating 2 on matrix 1. The analyte 8 is attached to the acceptor molecule 4. The acceptor molecule 4 receives the energy transfer from the surface coating 2. This is shown in the diagram by an arrow. The immunoassay is designed in a way to detect that presence and quantity of the analyte 8 the may exist in solution. The invention has the ability to improve both intensity and lifetime fluorescence measurements.

EXAMPLE 2

Figure 4B:
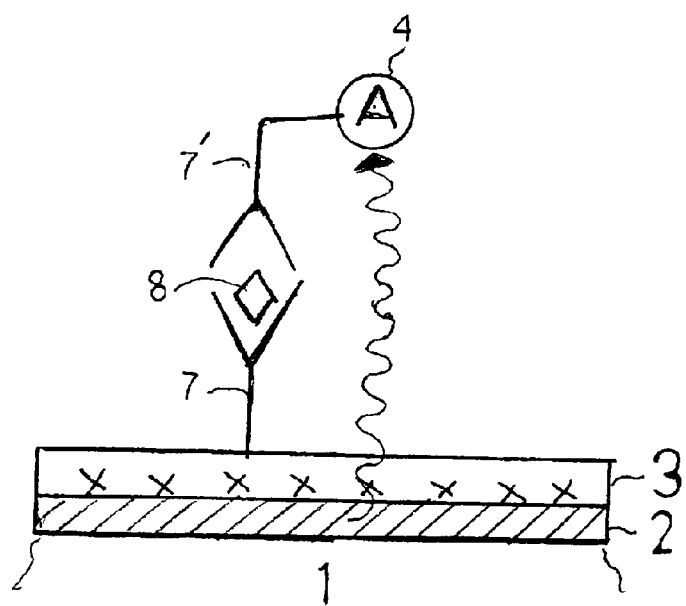
FIG. 4B shows a second embodiment and method of the present invention using a sandwich immunoassay.

In an alternative embodiment, after incubation with the sample to form the donor-tagged antibody analyte immuno-complex, an acceptor-tagged antibody is introduced to form a sandwich complex (See FIG. 4B). The methods and chemistries for the sandwich complex formation are well known in the art of immunochemistry. The second antibody, tagged with the acceptor molecule, presents the acceptor in such a way that the fluorescence emitted by the donor is quenched. The number of quenching events is proportional to the analyte concentration. Thus, the lifetime and intensity of the fluorescence decreases in proportion to the amount of analyte in the sample.

FIG. 4B shows a second method and embodiment of the invention except with a sandwich assay or immunoassay. In this case the existence and quantity of the analyte 8 is determined by the binding of the antibody 7' with the acceptor 4 and the antibody 7 with the analyte 8. In other words, the analyte is sandwiched between the antibodies 7 and 7'. Energy is transferred from the surface coating 2 to the acceptor 4 attached to the antibody 7' that has become bound to the analyte 8.

EXAMPLE 3

Each of the above embodiments of the invention teaches applications with immunoassays. However, this invention can be applied to a number of different assays. These assays include DNA hybridization detection, detection of any receptor binding to its complement, and detection of cleavage of a bond linking a group carrying the acceptor to a group carrying a donor etc. For example, one could design assays for detection of an inclusion compound complexing with a receptor molecule. In another embodiment this invention can be practiced for determining activity of a protease molecule. For example a substrate molecule can be tagged with the acceptor in a way that there is net energy transfer from the donor to the acceptor. Now if a protease molecule cleaves a site on the substrate somewhere between the acceptor and the donor, the two tags will be separated substantially and there will be no net energy transfer. Such a scheme can be used to determine the activity of a protease molecule at intervening sites on the substrate (See FIG. 3 for an illustration). Other embodiments could also include the use of the method with DNA or RNA as a probe or with aptamers for protein binding. These novel methods are discussed in more detail below.

Figure 4C:
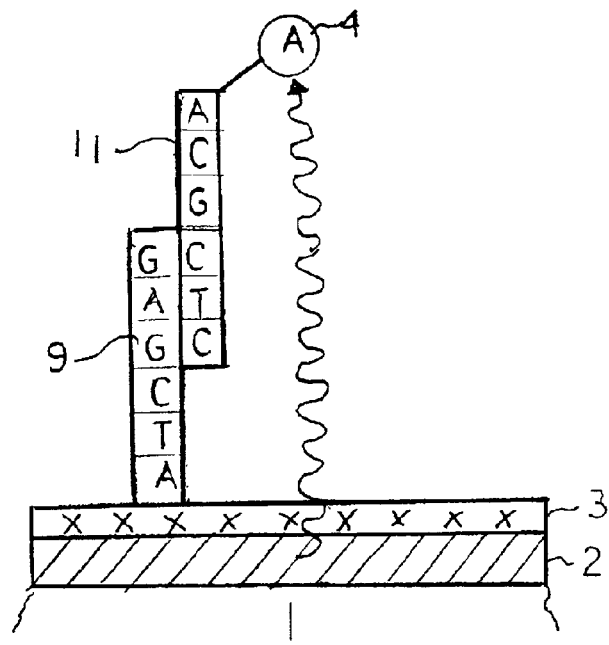
FIG. 4C shows a third embodiment and method of the present invention using a nucleic acid probe.

FIG. 4C shows another embodiment of the invention except in this case an RNA or DNA probe is used. The diagram depicts a situation where not all the nucleotides base pair. The invention, however, includes the situation when all the nucleotides of the probe and target base pair as well as partial base pair. The DNA or RNA probe 9 is attached to the protection layer 3. The DNA or RNA probe 9 can be a known or unknown sequence and can be used to bind other nucleotides 11 that have been covalently attached to the acceptor molecule 4. This type of assay can then be used to effectively monitor the quantity of nucleotides 11 that are free in solution or bound to the DNA or RNA probe 9. The arrow in the diagram shows how the energy can be transferred from the surface coating 2 to the acceptor 4. This embodiment or similar type embodiments have the capability of being applied to a variety of technologies including micro-arrays.

Figure 4D:
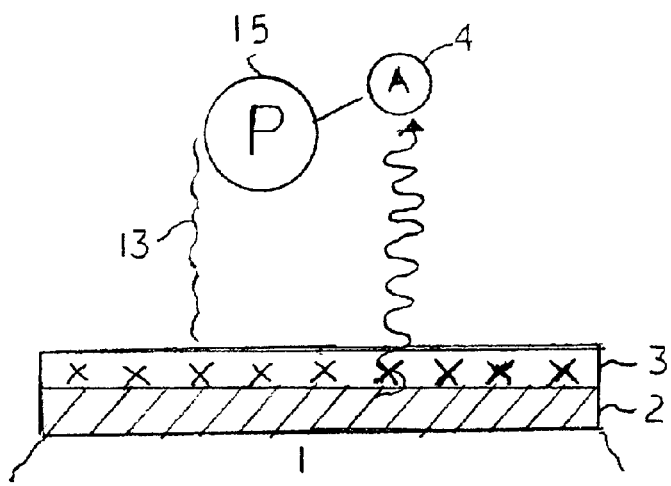
FIG. 4D shows a fourth embodiment and method of the present invention using an aptamer and protein.

FIG. 4D shows another embodiment of the present invention. In this case, an aptamer 13 is attached to the protection surface 3 that is capable of binding a protein 15 with an attached acceptor molecule 4. When the protein 15 contacts the aptamer 13 it is bound so that the acceptor molecule 4 is in close proximity to the surface coating 2. The arrow in the diagram shows how energy transfer takes place from the surface coating 2 to the acceptor 4 that is bound to the protein 15. This embodiment or similar type embodiments have the capability of being applied to a variety of technologies including micro-arrays.

Figure 4E:
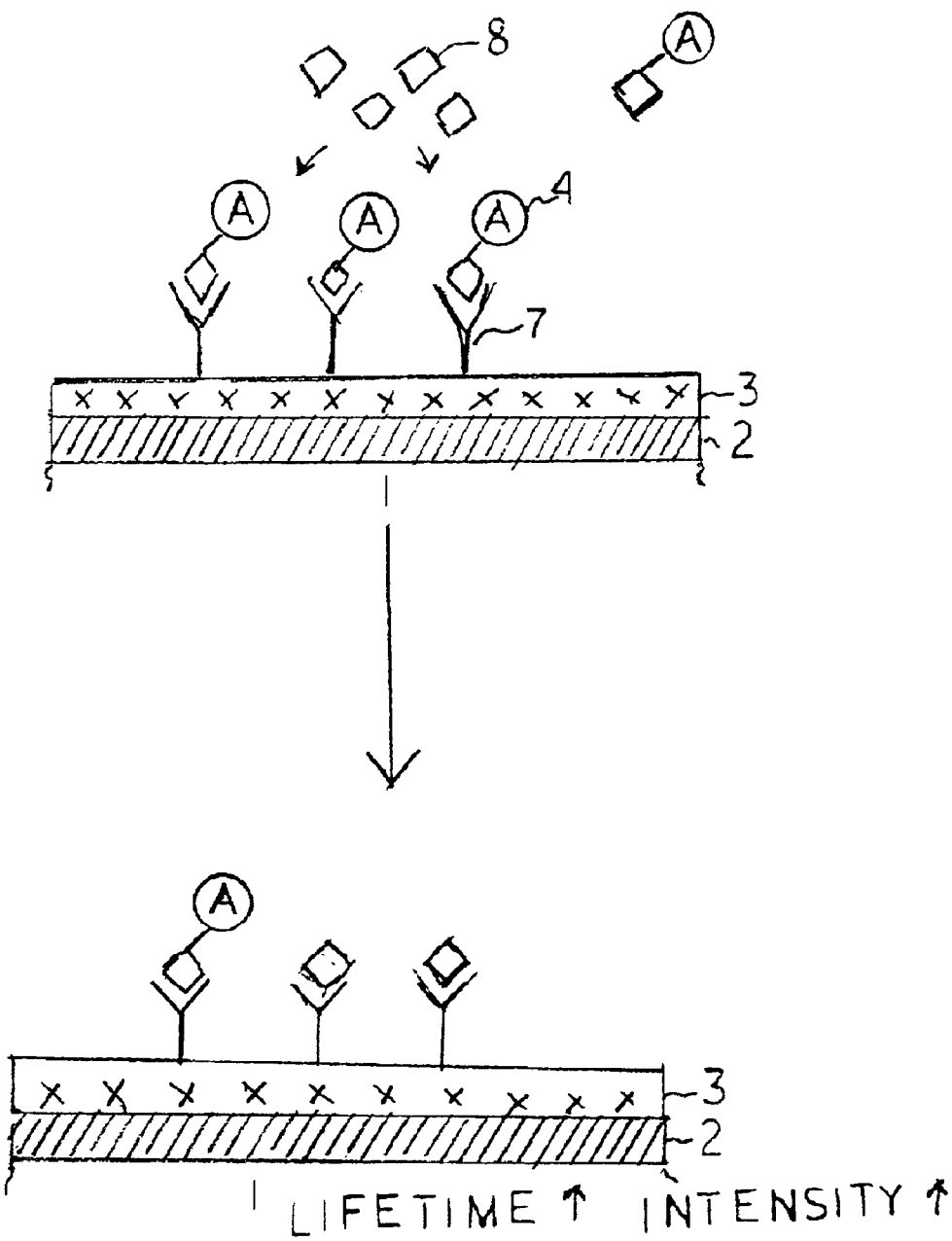
FIG. 4E shows a fifth embodiment and method of the present invention.

FIG. 4E shows an embodiment similar to the 4A embodiment. However, excess analyte 8 is present in solution. The analyte 8 with bound acceptor 4 competes for binding to the antibody 7 with the analtye 8 without bound acceptor. Lower energy transfer results when less analyte with bound acceptor binds to the antibody 7.

A number of photoluminescent donors may be used in the method of the invention and include the compounds listed above as well as groups such as cyanines, oxazines, thiazines, porphyrins, phthalocyanines, fluorescent infrared-emitting polynuclear aromatic hydrocarbons, phycobiliproteins, squaraines and organo-metallic complexes.

In the method, a number of important acceptors may be used in conjunction with the acceptors described above for the composition. For instance, some of the photoluminescent acceptors may also include the cyanines, oxazines, thiazines, porphyrins, phthalocyanines, fluorescent infrared-emitting polynuclear aromatic hydrocarbons, phycobiliproteins, squaraines, organo-metallic complexes, and azo dyes.

We claim:

1. An encapsulation vesicle, comprising:
   (a) a synthetic polymeric matrix having a surface;
   (b) a surface coating on said matrix, wherein said surface coating comprises a fluorescent molecule that is an organo-metallic complex; and
   (c) a protection layer encapsulating said surface coating, wherein said protection layer permits at least partial transmission of fluorescence emission from said fluorescent molecule upon irradiation of said fluorescent molecule, and wherein said protection layer reduces quenching of said fluorescent molecule and is capable of excluding small molecules.

2. An encapsulation vesicle as recited in claim 1, wherein said matrix comprises a sol-gel material.

3. An encapsulation vesicle as recited in claim 1, wherein said matrix comprises silica and synthetic polymer.

4. An encapsulation vesicle as recited in claim 1, wherein said fluorescent molecule is an organo-metallic complex, and wherein the matrix surface is modified with carboxyl groups so that the organo-metallic complex can be covalently attached to the matrix surface.

5. An encapsulation vesicle as recited in claim 1, wherein said fluorescent molecule is an organo-metallic complex, and wherein the matrix surface is modified with amino groups so that the organo-metallic complex can be covalently attached to the matrix surface.

6. An encapsulation vesicle as recited in claim 1, wherein said organo-metallic complex is a ruthenium tris diphenyl phenanthroline complex.

7. An encapsulation vesicle as recited in claim 1, wherein said organo-metallic complex has an emission maximum at about 650 nm.

8. An encapsulation vesicle as recited in claim 1, wherein said fluorescent molecule is selected from the group consisting of:

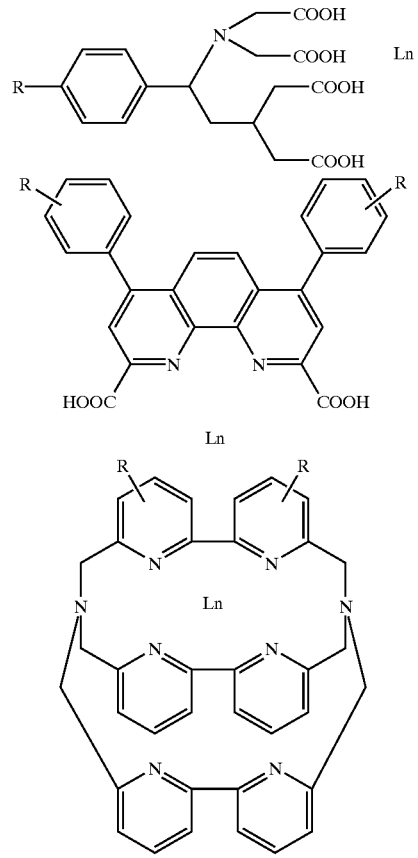

where Ln is selected from the group consisting of Eu, Tb, Sm, and Dy; and R represents H or a functionality capable of covalently linking to the surface of said matrix.

9. An encapsulation vesicle as recited in claim 1, wherein said fluorescent molecule has a fluorescence lifetime greater than 100 nanoseconds and is susceptible to collisional quenching by oxygen.

10. An encapsulation vesicle as recited in claim 2, wherein said protection layer comprises a material that is translucent to said fluorescence.

11. An encapsulation vesicle as recited in claim 2, wherein said protection layer comprises a material that is transparent to said fluorescence.

12. An encapsulation vesicle as recited in claim 2, wherein said protection layer comprises a sol-gel material.

13. An encapsulation vesicle as recited in claim 2, wherein said protection layer is modified with hydrophilic functionalities selected from the group consisting of hydroxyl, carboxyl and protonated amines.

14. An encapsulation vesicle as recited in claim 2 that was formed by suspension polymerization.

15. An encapsulation vesicle as recited in claim 1 further comprising a ligand attached to said protection layer.

16. An encapsulation vesicle as recited in claim 15, wherein said ligand comprises an acceptor molecule that is capable of absorbing fluorescence that has been emitted from said fluorescent molecule.

17. An encapsulation vesicle as recited in claim 1 further comprising an antibody linked to said protection layer.

18. An encapsulation vesicle as recited in claim 16, wherein an absorption band of said acceptor molecule overlaps with an emission band of said fluorescent molecule.

19. An encapsulation vesicle as recited in claim 16, wherein said acceptor molecule is selected from the group consisting of fluorescein Cy5 and allophycocyanin.

20. An encapsulation vesicle as recited in claim 15, wherein said ligand is an antibody.

21. An encapsulation vesicle as recited in claim 15, wherein said ligand is selected from the group consisting of proteins, DNA, RNA, polypeptides, aptamers and receptor molecules.

22. An encapsulation vesicle as recited in claim 17, wherein said vesicle is configured for use in a fluorescence energy transfer immunoassay.

23. An encapsulation vesicle as recited in claim 1 further comprising a polynucleotide linked to said protection layer.

24. An encapsulation vesicle as recited in claim 1 further comprising a ligand linked to said protection layer.

25. An encapsulation vesicle as recited in claim 1 further comprising an aptamer linked to said protection layer.

26. An encapsulation vesicle as recited in claim 15, wherein said ligand is an antigen.

27. An encapsulation vesicle as recited in claim 2, wherein said protection layer comprises silica and synthetic polymer.

28. An encapsulation vesicle as recited in claim 16, wherein said acceptor molecule is selected from the group consisting of Fast green and Light green SF yellowish.

29. An encapsulation vesicle as recited in claim 16, wherein said acceptor molecule is selected from the group consisting of cyanines, oxazines, thiazines, porphyrins, phthalocyanines, fluorescent infrared-emitting polynuclear aromatic hydrocarbons, phycobiliproteins, squaraines, organo-metallic complexes, and azo dyes.

30. An encapsulation vesicle as recited in claim 1 further comprising an acceptor molecule attached to said protection layer, wherein said acceptor molecule is capable of absorbing fluorescence that has been emitted from said fluorescent molecule.

31. An encapsulation vesicle as recited in claim 30, wherein said acceptor molecule is selected from the group consisting of Fast green and Light green SF yellowish.

32. An encapsulation vesicle as recited in claim 30, wherein said acceptor molecule is selected from the group consisting of fluorescein, Cy5 and allophycocyanin.

33. An encapsulation vesicle as recited in claim 30, wherein said acceptor molecule is selected from the group consisting of cyanines, oxazines, thiazines, porphyrins, phthalocyanines, fluorescent infrared-omitting polynuclear aromatic hydrocarbons, phycobiliproteins, squaraines, organo-metallic complexes, and azo dyes.

34. An encapsulation vesicle as recited in claim 30, wherein an absorption band of said acceptor molecule overlaps with an emission band of said fluorescent molecule.

35. An encapsulation vesicle as recited in claim 1, wherein said fluorescent molecule is susceptible to collisional quenching by oxygen and said protection layer reduces the diffusion of oxygen into said surface coating.

36. An encapsulation vesicle as recited in claim 1, wherein said fluorescent molecule is:

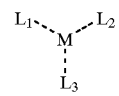

where M is selected from the group consisting of Ru, Os and Re; and $L_1$–$L_3$ are each independently selected from the group consisting of:

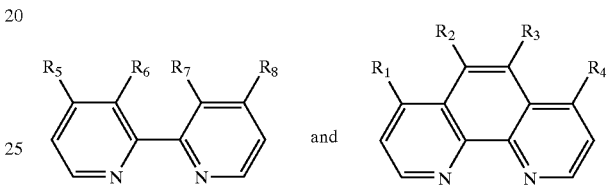

where $R_1$–$R_8$ are each independently selected from the group consisting of H, alkyl and aryl.

37. An encapsulation vesicle as recited in claim 1, wherein said fluorescent molecule is:

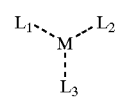

where M is Os;
$L_1$ is:

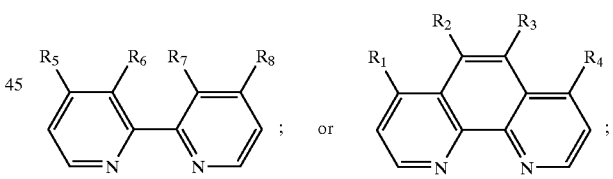

and $L_2$ and $L_3$ are independently selected from the group consisting of:

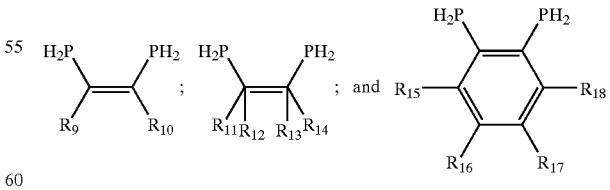

where $R_1$–$R_{18}$ are each independently selected from the group consisting of H, alkyl, and aryl.

38. An encapsulation vesicle as recited in claim 1, wherein said protection layer comprises a sol-gel.

* * * * *